United States Patent [19]

Margaria et al.

[11] Patent Number: 5,714,131
[45] Date of Patent: Feb. 3, 1998

[54] METALLURGICAL SILICON CONTAINING PHOSPHORUS FOR THE PREPARATION OF ORGANOHALOGENOSILANES

[75] Inventors: Thomas Margaria, Chedde, France; Bruno Degen, Much, Germany; Elke Licht, Leverkusen, Germany; Manfred Schulze, deceased, late of Leichlingen, Germany, by Elke Lotte Hildegard Schulze, heir; Gebhard Wagner, Odenthal, Germany

[73] Assignees: Pechiney Electrometallurgie, Courbevoie, France; Bayer AG, Leverkusen, Germany

[21] Appl. No.: 553,548

[22] PCT Filed: Jun. 30, 1994

[86] PCT No.: PCT/FR94/00799

§ 371 Date: Dec. 15, 1995

§ 102(e) Date: Dec. 15, 1995

[87] PCT Pub. No.: WO95/01303

PCT Pub. Date: Jan. 12, 1995

[30] Foreign Application Priority Data

Jul. 1, 1993 [FR] France .................. 93 08303

[51] Int. Cl.$^6$ ........................................ C01B 33/02
[52] U.S. Cl. ............................... 423/348; 556/472
[58] Field of Search ......................... 423/348; 556/472

[56] References Cited

U.S. PATENT DOCUMENTS

| 2,877,254 | 3/1959 | Enk et al. ................. 556/472 |
| 4,304,763 | 12/1981 | Dietl et al. ............... 423/348 |
| 4,500,724 | 2/1985 | Ward, III et al. ........ 556/472 |
| 4,534,791 | 8/1985 | More et al. .............. 423/348 |
| 4,602,101 | 7/1986 | Halm et al. .............. 556/472 |
| 4,898,960 | 2/1990 | Dosag et al. ............. 556/472 |
| 5,334,738 | 8/1994 | Pachaly et al. ......... 556/472 |
| 5,605,583 | 2/1997 | Margaria ................. 423/348 |

FOREIGN PATENT DOCUMENTS

| 0272860 | 6/1988 | European Pat. Off. ... 556/472 |
| 0273635 | 7/1988 | European Pat. Off. ... 556/472 |
| 0372918 | 6/1990 | European Pat. Off. . |
| 2556333 | 6/1985 | France . |
| 1165026 | 3/1964 | Germany . |
| 157349 | 10/1963 | U.S.S.R. . |
| 681387 | 10/1952 | United Kingdom ..... 556/472 |
| 590458 | 7/1974 | United Kingdom ..... 423/348 |

OTHER PUBLICATIONS

Lobusevich et al. "Influence of Addition . . . with Methyl Chloride", Journal of General Chemistry of the USSR—A Translation of Zhurnal Obshchei Khimii, vol. 34, No. 8, Aug. 1964, pp. 2727–2729.

Margaria et al. "Intermetallic Compounds in Metallurgical Silicon", INFACONG, Proceedings of the 6th International Ferroalloys Congress, Capetown, vol. 1, Johannesburg, 1992 (no month) pp. 209–214.

*Primary Examiner*—Ngoc-Yen Nguyen
*Attorney, Agent, or Firm*—Dennison, Meserole, Pollack & Scheiner

[57] ABSTRACT

A metallurgical silicon is disclosed which contains substantially from 30 to 180 ppm of phosphorus comprised of a crystalline phase of primary silicon having a dissolved phosphorus content between 30 and 150 parts per million and intermetal phases whose global ratio is between 0.5 and 2%, wherein among the intermediary phases, the phase $Si_2Al_2Ca$ does not exceed 0.3% of the total of the metallurgical silicon mass. The metallurgical silcon is used for the synthesis of alkyl or aryl halogenosilanes useful for the preparation of silicones.

8 Claims, No Drawings

METALLURGICAL SILICON CONTAINING PHOSPHORUS FOR THE PREPARATION OF ORGANOHALOGENOSILANES

FIELD OF THE INVENTION

The innovation relates to a particular type of metallurgical silicon having a controlled structure and containing a controlled quantity of phosphorus whose distribution in the various phases which constitute the structure of the metallurgical silicon is itself controlled.

This type is particularly well adapted to the synthesis reaction of alkyl or aryl halogenosilanes.

DESCRIPTION OF RELATED ART

The synthesis of alkyl or aryl halogenosilanes (which will hereinafter be called "silanes") through the reaction of a halogenated hydrocarbon with silicon in the presence of a copper-based catalyst at a temperature of 250° to 350° C. is known from U.S. Pat. No. 2,380,995 granted to Rochow on Aug. 7, 1945.

This reaction, hereinafter referred to as "the Rochow reaction", has undergone considerable industrial development, having been in particular the basis for the entire silicone industry.

This reaction is generally produced with methyl chloride $CH_3Cl$ and results in a mixture of various methyl chlorosilanes, particularly monomethyltrichlorosilane $CH_3SiCl_3$ (which will hereinafter be called T) and dimethldichlorosilane $(CH_3)_2SiCl_2$ (which will hereinafter be called D). Since the most sought-after product is D, it is very important to be able to control the reaction in such a way as to obtain the maximum proportion of D in the mixture of silanes obtained, a ratio which is called selectivity. It is also very important to be able to produce the maximum quantity of silanes per unit of time, the value of the weight flow of silanes produced being called reactivity.

Since the initial Rochow patent of 1945, a vast amount of work has been devoted to increasing the reactivity and selectivity of the Rochow reaction. Research had been conducted on the technology of the process—which, while originally carried out in a fixed bed, is now almost always done in a fluidized bed—on the physical form of the silicon used (particle size distribution, etc . . .) and particularly on the catalytic systems used, and on the chemical composition of the silicon, this silicon being an industrial product which contains a certain number of impurities.

U.S. Pat. No. 4,602,101 granted to Halm et al on Jul. 22, 1986, provides (columns 1 through 4) a fairly extensive summary of the knowledge of the catalytic systems studied. This summary shows that a certain number of elements or compounds have been described as catalysts of the Rochow reaction, while others have been indicated as cocatalysts or catalyst promoters because their use in conjunction with certain catalysts makes it possible to improve selectivity and/or reactivity.

The original catalyst, copper, is the most often cited and is utilized universally. However, nickel, antimony, manganese, silver, titanium and iron are also cited as catalysts. Copper can be used either in metallic form or in the form of oxides (possibly formed in situ from other derivatives such as copper nitrate), or in the form of halides.

It is possible to add promoters to these catalysts, or to some of them, which can either be elements such as:

zinc, cadmium, mercury;

tin, particularly in the presence of copper or copper and zinc;

the metals from group VII of the periodic table of the elements;

phosphorus or certain phosphorus-containing derivatives; or compounds such as:

copper oxides or other catalyst metals;

metal hydroxides from group IV of the periodic table of the elements, used with copper;

refractory hydrous oxides, for example hydrous aluminas, used with copper;

copper, iron, or zinc halides or other copper salts (formate), used with copper and/or its oxides, and sometimes with iron.

Some of these catalysts and promoters are particularly noteworthy, specifically copper as a catalyst and zinc, tin and phosphorus as promoters.

Since Jan. 15, 1954, the publication date of U.S. Pat. No. 2,666,776 (Nitzsche et al.), the beneficial influence of phosphorus as a cocatalyst or promoter has been recognized: column 1, lines 26–37, indicates that alkyl or aryl halides of silicon, particularly dialkyl or diarylhalogenosilanes, are obtained by using an alloy which contains, in addition to silicon and copper, a metal from the 5th or 8th group of the periodic table, particularly cobalt, nickel, iron or phosphorus, and that an additional increase in effectiveness is obtained if the catalyst is used in connection with an activation agent, for example a copper salt.

The importance of phosphorus was confirmed, first by Rossmy in his German patent 1 165 026 filed Sep. 14, 1959 and granted Mar. 12, 1964, and later by Trofimova in the Soviet application No. 754 859 filed Dec. 8, 1961, which resulted in the granting of the certificate of invention No. 157 349, said certificate being mentioned in the February, 1966, issue of "Soviet Invention Illustrated." This certificate mentions the utilization of a silicon-copper alloy which also contains antimony and phosphorus. In an example, it specifies a copper content of 10%, an antimony content of 40 ppm, and a phosphorus content of 200 ppm.

In an article published in Zhurnal Obshchei Khimii, Vol. 34, No. 8, pp. 2 706 through 2 708 (August 1964), Lobusevich, Trofimova et al. show that phosphorus used alone is a reaction poison in the presence of a copper catalyst, but that conversely, it results in an improvement in selectivity in the presence of other promoters, such as antimony, arsenic, zinc. This positive effect is optimal for a phosphorus content between 100 and 200 ppm.

Since these publications, there has been an effort to use phosphorus as a promoter in the Rochow reaction, and various formulas and techniques have been described, for example:

Ward, in his U.S. Pat. No. 4,500,724, describes the utilization of complex formulas comprising copper (or copper chloride), zinc, tin and phosphorus, which produce particularly advantageous results with regard to reactivity and selectivity;

Halm, in his above-mentioned U.S. Pat. No. 4,602,101, describes the utilization in the Rochow reaction of a promoter chosen from among elementary phosphorus, metallic phosphides, or compounds capable of forming metallic phosphides under the conditions of the reaction, in a quantity of 25 to 2,500 ppm relative to the silicon, in the presence of tin and copper;

For economic reasons, the silicon generally used in the Rochow reaction is a metallurgical silicon produced through carboreduction of silica in an electric furnace, then refined in order to adjust the ratio of its principal impurities, and finally cast into loaves and solidified. The solid mass is then reduced to a powder with a particle size distribution adapted for utilization in industrial silane production facilities. There are numerous monographs which relate to this technique of silicon production, one of which, for example, may be found in Chapter II, "Silicon Alloys," of the work by Elyutin et al., "Production of Ferroalloys-Electrometallurgy," published in English in Moscow in 1957 by "The State Scientific and Technical Publishing House for Literature on Ferrous and Non Ferrous Metallurgy."

This metallurgical silicon contains a certain number of principal impurities, essentially calcium, aluminum, and iron, all of which are present in proportions between 0.01 and 1%, proportions which are adjusted during the refining process in order to meet the specifications required by the market. It also contains secondary impurities contained in the raw materials, which the process of production and refining does not always make it possible to eliminate. These impurities, as well as the proportions of their presence in the silicon, generally between 10 and 500 ppm, greatly depends on the origin of the raw materials used. The most common of these impurities are metalloids, phosphorus, boron, sulfur, carbon, or metals, titanium, copper, magnesium, manganese, nickel, vanadium, zirconium, etc.

The source of the phosphorus content, as revealed in Chapter II of the above-mentioned work by Elyutin, pp. 65 through 68, is the various raw materials used in the production of metallurgical silicon, and it is shown in particular how the phosphorus content of the silicon produced can be determined from that of the various raw materials. The phosphorus contents usually encountered vary between 25–30 ppm and 400–500 ppm. The article "High-Purity Silicon for Solar Cell Application" by Dosaj et al. published by the Journal of Metals, June, 1978, in its Table VII on p. 12, gives a value of 50 ppm, the article "Efficient Polycrystalline Solar Cells Made from Low-Cost Refined Metallurgical Silicon," by Haneka et al., Thirteenth IEEE Photovoltaic Specialists Conference-1978, pages 485–9, published by the IEEE, New York, in 1978, in its Table I on p. 487, indicates a value of 100 ppm, and the above-mentioned work by Elyutin, on page 67, indicates a value of 400 ppm.

It is therefore absolutely certain that since the beginning of silane production, the phosphorus present in the silicon has made a contribution to the catalysis of the Rochow reaction, a variable and often random contribution depending on the phosphorus content of the silicon used, but an effective contribution for all silane producers.

Recently, Dosaj, Halm and Wilding obtained European patent 0 272 860, granted Oct. 7, 1992, while Halm and Wilding obtained European patent 0 273 635, granted Feb. 10, 1993. These two patents describe the utilization in the Rochow reaction of a silicon which contains from 25 to 2,500 ppm of a phosphorus-containing promoter in the presence of a catalyst which contains copper and tin, and possibly zinc. In European patent 0 272 860, this promoter is introduced into the silicon by choosing and metering raw materials in accordance with the method described in Chapter II, p. 65 through 68, of the above-mentioned work by Elyutin, whereas in European patent 0 273 635, the promoter is simply a nonvolatile phosphorus-containing compound added to the liquid silicon during its refining.

However, these techniques are not satisfactory, for it has become apparent that two samples of silicon containing the same quantity of phosphorus obtained through either one of these techniques could cause substantially different modifications in the selectivity and reactivity of the Rochow reaction, as will be shown below.

SUMMARY OF THE INVENTION

During research intended to eliminate or at least reduce these non-reproducible results, Applicant have found that metallurgical silicon was constituted by various phases, the principal one of which is a very pure crystallized silicon phase, referred to below as primary silicon, in which only two dissolved impurities, boron and phosphorus, can exist, the other phases being constituted by various combinations of silicon and principal and secondary impurities.

Applicant have also found that the phosphorus present in metallurgical silicon was distributed among the various phases present, particularly between the dominant phase of primary silicon and, when it exists, a ternary $Si_2Al_2Ca$ phase.

The invention relates to a type of metallurgical silicon which is particularly well adapted to the Rochow reaction with its improved characteristics of selectivity and reactivity, characterized by the presence of 30 to 150 ppm phosphorus in the dominant phase of primary silicon and by the absence or near-absence of a ternary $Si_2Al_2Ca$ phase whose quantity relative to the total mass of metallurgic silicon must not exceed 0.3%.

The invention also relates to a process for preparing a product of this type.

DETAILED DESCRIPTION OF THE INVENTION

The various intermetallic phases which can exist in metallurgical silicon in addition to the dominant phase of primary silicon were described by Margaria et al. in "Proceedings of the 6th International Ferroalloys Congress Cape Town," Vol. 1, Johannesburg, SAIMM, 1992, pp. 209 through 214. There are seven principal phases to which secondary phases are added which depend on the secondary impurities which are effectively present, only one of which ($Si_2Al_2Ca$) is capable of including appreciable quantities of phosphorus, as shown by Tables I and II, p. 210. This article shows how these intermetallic phases are created during the solidification process of the metallurgical silicon, and how they are deposited at the grain boundaries of the dominant phase. Also, on p. 210, it provides a means of analysis by which, using images from electron microscopy and X-ray diffraction, it is possible to discover the spatial distribution of the various phases and their composition.

These same techniques, combined with a complex mathematical process, can be used to evaluate the respective ratio of each of the phases in the metallurgical silicon studied. Generally, the aggregate proportion of all the intermetallic phases is between 0.5 and 2% and essentially depends on the proportions of the principal impurities which are adjusted during the refining process.

The total quantity of phosphorus introduced into the metallurgical silicon during its preparation, whether through the raw materials or through any other addition, are distributed, as indicated in the above-mentioned article by Margaria, between the dominant phase and the $Si_2Al_2Ca$ phase, the other intermetallic phases not being able to accept significant fractions of it. Thus, it was also found, for example, that in a metallurgical silicon which contained 200 ppm phosphorus total, the dominant phase of primary silicon would only contain 50 ppm phosphorus, while the $Si_2Al_2Ca$ phase, present at a proportion of 1.5%, would contain 10,000 ppm phosphorus.

Applicants have found that, surprisingly, the quantities of phosphorus contained in the dominant phase and in the $Si_2Al_2Ca$ phase did not have the same effect on the modification of the selectivity and reactivity of the Rochow reaction. The silicon contained in the dominant phase of primary silicon has a beneficial effect on selectivity and reactivity as long as its ratio is between 30 and 150 ppm, its effect being insignificant below 30 ppm and becoming harmful, decreasing selectivity, as the ratio increases beyond 150 ppm. These results are comparable to those obtained by Lobusevich and Trofimova in the above-mentioned article, the phosphorus in that case apparently having been added at the moment of the reaction rather than being added to the silicon used.

The phosphorus contained in the $Si_2Al_2Ca$ phase, on the other hand, does not have a positive effect by itself. On the contrary, it contributes to a degradation of the selectivity, which actually seems to depend on the total quantity of phosphorus contained in the metallurgical silicon.

In summary, metallurgical silicon with the same aggregate chemical composition, particularly where its proportion of phosphorus is concerned, will produce substantially different results in the Rochow reaction, depending on the distribution of the phosphorus it contains between the dominant phase of primary silicon and the intermetallic $Si_2Al_2Ca$ phase, the other intermetallic phases having no notable effect.

The silicon which leads to the best results in the Rochow reaction is a silicon containing between 30 and 180 ppm phosphorus. Almost all of this phosphorus is contained in the dominant phase of primary silicon. The rest, namely a maximum of about 30 ppm, is linked to the $Si_2Al_2Ca$ phase, which can contain 10,000 ppm but in which its content is limited to 0.3% of the weight of the silicon. This result can be obtained by controlling the total quantity of phosphorus introduced into the metallurgical silicon through its raw materials, as well as the quantity which may specifically be added to the liquid silicon during its production, its furnace casting, its refining, or its final casting, and also by controlling the formation of the $Si_2Al_2Ca$ phase so as to limit it to a maximum of less than 0.3%, for example, and preferably less than 0.1%.

To obtain this type of silicon, it is possible to use the usual process for producing metallurgical silicon through the carboreduction of silica in an electric furnace, the raw materials being chosen by the method described in the above-mentioned work by Elyutin et al. in order to endow the product obtained with a specific total proportion of phosphorus, a proportion which is capable of being adjusted to the desired value between 30 and 180 ppm by adding a nonvolatile compound of phosphorus, such as tricalcium phosphate to the liquid silicon at any moment.

This silicon is then refined in the liquid phase by means of a standard treatment with the aid of an oxidizing agent, for example oxygen or air, which partially eliminates some of the most oxidizable impurities such as aluminum and calcium, the majority of the impurities, particularly the phosphorus, being unaffected and remaining in the liquid phase.

It is then cast in the form of ingots which, as seen above, include a dominant phase of primary silicon containing as impurities only phosphorus and boron and various intermetallic phases situated at the grain boundary of the dominant phase.

To control the presence of the $Si_2Al_2Ca$ phase and to limit it to 0.3%, preferably 0.1%, it is possible to simply cool the cast mass very slowly, particularly when passing through the sensitive zone from 1200° C. to 800° C., as indicated in the above-mentioned article by Margaria, page 213. However, this technique has industrial disadvantages due to its slowness and to the fact that in a massive ingot it results in a structure that is too heterogeneous.

In order to obtain the desired structure (limitation of the $Si_2Al_2Ca$ phase to 0.3% and preferably to 0.1%) throughout the solidified mass using industrial solidification processes, two conditions will be satisfied simultaneously: one of these consists of adjusting the ratio of the impurities Fe, Al, Ca in the silicon to within a very precise range; the other consists of determining the conditions for solidification. In general, the range of composition is chosen as a function of the solidification speeds which are effectively realized.

The desired result can thus be obtained by simultaneously adjusting two weight ratios:

—the ratio of the sum of the weight percentages of aluminum and calcium to the weight percentage of iron in the silicon, (Al+Ca)/Fe. This ratio would have to be between 0.7 and 0.9 for slow solidification speeds, that is, such that the temperature is reduced from 1000° C. to 800° C. at a rate between 6° and 30° C./min. This ratio would have to be between 0.5 and 0.7 for rapid solidification speeds, that is, such that the temperature is reduced from 1000° C. to 800° C. at a rate between 30° and 120° C./min.

—the ratio of the weight percentage of aluminum to that of calcium in the silicon, Al/Ca, which would have to be between 2.5 and 4.5, and preferably between 3.3 and 3.7.

This adjustment of these two weight ratios can advantageously be carried out during the oxidizing refining of the silicon, which consists of injecting air and/or oxygen into the molten silicon. This refining reduces the calcium and aluminum contents by adjusting the quantity and the duration of action of the oxidizing agent until the desired weight ratios are obtained and if necessary, by adding more of either of these two elements if its elimination has been excessive.

The silicon whose characteristics and production process has been described above finds application in the direct, so-called Rochow reaction for producing alkyl or aryl halogenosilanes through a reaction with alkyl or aryl halides at a temperature between 250° and 350° C., in the presence of a copper-containing catalyst and possibly one or more promoters: tin, zinc, antimony.

EXAMPLES

Example 1

Production of an Si which has an excessive $Si_2Al_2Ca$ content.

The silicon is produced through carbothermy in a reduction furnace from silicas and reducing agents: coals, cokes, woods, charcoals. This original silicon, including the raw materials used, contains 0.28% iron, 0.7% Ca, 0.6% aluminum and 90 ppm phosphorus.

This silicon is then subjected to an oxidizing refining in a ladle through an addition of silica and an injection of air and/or oxygen intended to reduce the calcium and aluminum contents. Thus a silicon is obtained which contains 0.28% iron, 0.080% calcium, 0.12% Al. The phosphorus not affected by the refining retains a content of 90 ppm. Next, 1.6 kg of aluminum and 0.5 kg of a CaSi alloy having 30% calcium is added per ton of liquid Si. The liquid alloy, homogenized by an insufflation of nitrogen, is then cast and solidified into ingots with a thickness of 10 cm on the one hand, and ingots with a thickness of 20 cm on the other hand, in cast iron ingot molds.

After a representative sampling of the solid silicon, an analysis shows that this silicon contains 0.31% iron, 0.26% aluminum, 0.09% calcium, 90 ppm phosphorus.

According to these analyses, on the one hand, (Al+Ca)/Fe=1.13 and Al/Ca=2.8.

A ground section of the silicon thus obtained is examined with the aid of a scanning electron microscope connected to an image analysis system.

Thus it is possible to identify the $Si_2Al_2Ca$ phase from among the various intermetallic phases and to determine its proportion.

The results of these tests show that the $Si_2Al_2Ca$ phase has a total content of 0.15% which can reach 0.3% locally in the silicon cast in ingots with a thickness of 20 Cm, and has a total content of 0.2% which can reach 0.4% locally in the silicon cast in ingots with a thickness of 10 cm.

The microanalyses carried out with the aid of an electron microprobe show that the P content of the $Si_2Al_2Ca$ phase reaches 1.2% and that the primary silicon crystal has phosphorus contents which vary from 50 to 70 ppm for silicon cast in ingots with a thickness of 20 cm and which vary from 40 to 60 ppm for silicon cast in ingots with a thickness of 10 cm.

Example 2

Production of a silicon according to the invention which contains little $Si_2Al_2Ca$.

A silicon containing 0.35% iron, 0.05% calcium, 0.12% Al is produced in a reduction furnace with subsequent refining as described above. Next, 1.4 kg of aluminum and 0.6 kg of a 30% Ca CaSi alloy is added per ton of liquid silicon. The liquid alloy, homogenized by an insufflation of nitrogen, is then cast and solidified into ingots with thicknesses of 10 and 20 cm in cast iron ingot molds.

After a representative sampling of the solid silicon, an analysis shows that this silicon contains 0.35% iron, 0.25% aluminum, 0.06% calcium, 90 ppm phosphorus.

According to these analyses, on the one hand, (Al+Ca)/Fe=0.88, and Al/Ca=4.2.

The tests described above show that the $Si_2Al_2Ca$ phase is absent from the silicon cast into ingots with a thickness of 20 cm and has a total content of 0.1% which can reach 0.2% locally in the silicon cast into ingots with a thickness of 10 cm.

Microanalyses of the silicon show that the crystal of primary silicon has phosphorus contents of 90 ppm for the silicon cast in ingots with a thickness of 20 cm and contents which vary from 55 to 70 ppm for the silicon cast in ingots with a thickness of 10 cm.

Example 3

Production of a silicon according to the invention which does not contain any $Si_2Al_2Ca$.

A silicon containing 0.37% iron, 0.05% calcium, 0.10% Al is produced in a reduction furnace with a subsequent refining as described above. Next, 1 kg of aluminum and 0.6 kg of a 30% Ca CaSi alloy is added per ton of liquid silicon. The liquid alloy, homogenized by an insufflation of nitrogen, is then cast and solidified into ingots with thicknesses of 10 and 20 cm in cast iron ingot molds.

After a representative sampling of the solid silicon, an analysis shows that this silicon contains 0.37% iron, 0.19% aluminum, 0.06% calcium and 90 ppm phosphorus.

According to these analyses, on the one hand, (Al+Ca)/Fe=0.67 and Al/Ca=3.2, values which conform to the recommendations of the present invention.

The same test as that conducted in the two preceding examples did not detect the presence of a $Si_2Al_2Ca$ phase, either in the silicon cast into ingots with a thickness of 20 cm or in the silicon cast into ingots with a thickness of 10 cm.

The microanalyses of the silicon show that the crystals of primary silicon contain from 85 to 90 ppm phosphorus in both cases: therefore, the totality of the primary silicon effectively contains the desired concentration of phosphorus.

Example 4

This example shows the advantage of the presence of a sufficient quantity of phosphorus in the primary phase, obtained through the absence of a $Si_2Al_2Ca$ phase, in the synthesis of methylchlorosilanes.

Two samples of silicon 1 and 2 having the same phosphorus content - - - 30 parts per million - - - were compared; the analyses were the following:

| Sample | 1 | 2 |
|---|---|---|
| Fe (%) | 0.37 | 0.41 |
| Al (%) | 0.4 | 0.17 |
| Ca (%) | 0.18 | 0.054 |
| Ti (%) | 0.024 | 0.028 |
| P (ppm) | 30 | 30 |
| (Al + Ca)/Fe | 1.57 | 0.55 |
| Al/Ca | 2.22 | 3.15 |

Sample 1, according to its analysis, contains 0.36% $Si_2Al_2Ca$; the primary silicon contains only 5 to 10 ppm phosphorus and the sample is therefore not in conformity with the invention.

Sample 2, by reason of its analysis and its mode of cooling, is in conformity with the invention: it does not contain any $Si_2Al_2Ca$ and the concentration of phosphorus in the primary silicon is equal to the total content, namely 30 ppm.

Both of these samples were subjected to a methylchlorosilane production test under the following conditions:

The tests were conducted in a fluidized bed in a glass reaction vessel with a diameter of 30 mm equipped with an agitator. The same quantity of silicon having the same particle size distribution, between 71 and 160 µm, was used in each test. The reaction mixture contained 40 g of silicon, 3.2 g of partially oxidized copper as a catalyst, and 0.05 g of ZnO.

Methyl chloride was added to the reaction mixture through a sintered glass disk at a pressure of 2 bars. The quantity of methyl chloride was kept constant at 1.8 liters/h, measured at a pressure of 2 bars. After the reaction medium was heated and the reaction started, the temperature of the system was adjusted and maintained at 300° C. and the quantity and composition of the silane mixture formed was determined. The values indicated in the table below are the averages of 4 individual measurements.

In this table, P indicates the quantity of silanes produced in g/hour; MeH, Mono, T, D, PS indicate the respective percentages by weight of monomethyldichlorosilane ($CH_3HSiCl_2$), trimethylchlorosilane (($CH_3)_3SiCl$), methyltrichlorosilane ($CH_3SiCl_3$), dimethyldichlorosilane (($CH_3)_2SiCl_2$) and finally polysilanes. Since dimethyldichlorosilane is the desired product, the selectivity is estimated from the value of D, which must be as high as possible, and from that of T/D, which must be as low as possible.

| Smpl. | P (g/h) | MeH (%) | Mono (%) | T (%) | D (%) | T/D | PS (%) |
|---|---|---|---|---|---|---|---|
| 1 | 7.2 | 2.7 | 3.2 | 7.3 | 86.4 | 0.084 | 4.9 |
| 2 | 6.8 | 2.0 | 2.5 | 4.9 | 90.3 | 0.054 | 5.2 |

The gain in selectivity obtained with alloy 2 according to the invention is clear.

Example 5

This example shows that the results obtained in the synthesis of methylchlorosilane are similar, despite different total phosphorus contents, as long as these contents are similar in the primary silicon phase.

Two samples of silicon 3 and 4 having different phosphorus contents - - - 80 and 30 ppm - - - were compared, the analyses of which were the following:

| Sample | 3 | 4 |
| --- | --- | --- |
| Fe (%) | 0.29 | 0.41 |
| Al (%) | 0.32 | 0.17 |
| Ca (%) | 0.17 | 0.054 |
| Ti (%) | 0.019 | 0.028 |
| P (ppm) | 80 | 30 |
| (Al + Ca)/Fe | 1.69 | 0.55 |
| Al/Ca | 1.88 | 3.15 |

Sample 3, according to its analysis, contains 0.31% $Si_2Al_2Ca$; the primary silicon contains 40 ppm phosphorus and the sample is therefore not in conformity with the invention.

Sample 4, by reason of its analysis and its mode of cooling, is in conformity with the invention: it does not contain any $Si_2Al_2Ca$ and the concentration of phosphorus in the primary silicon is equal to the total content, namely 30 ppm, very near that of Sample 3.

Both of these samples were subjected to the same methylchlorosilane production test described in Example 4.

The results appear in the table below.

| Smpl. | P (g/h) | MeH (%) | Mono (%) | T (%) | D (%) | T/D | PS (%) |
| --- | --- | --- | --- | --- | --- | --- | --- |
| 3 | 6.1 | 1.8 | 2.3 | 5.4 | 90.3 | 0.059 | 3.6 |
| 4 | 6.8 | 2.0 | 2.5 | 4.9 | 90.3 | 0.054 | 5.2 |

It is noted that the selectivity performances obtained are similar to one another, which is due to the fact that the phosphorus content of the primary silicon is similar in both samples. On the other hand, it is noted that there is a slight degradation of reactivity in the sample having the higher total phosphorus content.

Example 6

This example allows a comparison of Samples 5, 6, 7, 8 in which there are successively higher phosphorus contents in the primary silicon. The first three contain the primary $Si_2Al_2Ca$ phase, the fourth does not.

The total phosphorus (Ptot) and the phosphorus content of the primary silicon (Pprim) were determined.

The analyses were the following:

| Sample | 5 | 6 | 7 | 8 |
| --- | --- | --- | --- | --- |
| Fe (%) | 0.37 | 0.29 | 0.29 | 0.38 |
| Al (%) | 0.4 | 0.3 | 0.32 | 0.15 |
| Ca (%) | 0.18 | 0.16 | 0.17 | 0.056 |
| Ti (%) | 0.024 | 0.019 | 0.019 | 0.022 |
| Ptot (ppm) | 30 | 50 | 80 | 90 |
| Pprim (ppm) | 10 | 30 | 50 | 90 |
| (Al + Ca)/Fe | 1.57 | 1.59 | 1.69 | 0.54 |
| Al/Ca | 2.22 | 1.875 | 1.88 | 2.68 |

Samples 5 through 7 are not in conformity with the invention. Only Sample 8 is.

Each of these samples was subjected to the same methylchlorosilane production test described in Example 4.

The results appear in the table below.

| Smpl. | P (g/h) | MeH (%) | Mono (%) | T (%) | D (%) | T/D | PS (%) |
| --- | --- | --- | --- | --- | --- | --- | --- |
| 5 | 7.2 | 2.7 | 3.2 | 7.3 | 86.4 | 0.084 | 4.9 |
| 6 | 6.0 | 2.3 | 2.3 | 5.2 | 89.8 | 0.057 | 2.8 |
| 7 | 6.1 | 1.8 | 2.3 | 5.4 | 90.3 | 0.059 | 3.6 |
| 8 | 5.4 | 1.9 | 1.0 | 3.7 | 93.2 | 0.039 | 2.7 |

It is clear that the selectivity performances obtained are particularly good in Sample 8 according to the invention. It is noted that Samples 7 and 8, in which the total phosphorus contents are similar, perform differently, which is linked to the different phosphorus contents in their primary Si phases.

We claim:

1. A metallurgical silicon comprising a crystalline phase of primary silicon having a dissolved phosphorus content between 30 and 150 ppm by weight and intermetallic phases in an amount of 0.5 to 2% by weight, said metallurgical silicon containing from 30 to 180 ppm by weight total phosphorus and not more than 0.3% by weight of an intermetallic $Si_2Al_2a$ phase, said silicon containing Al and Ca in a weight ratio Al/Ca which is between 2.4 and 4.5.

2. Silicon according to claim 1, wherein said metallurgical silicon contains not more than 0.1% by weight of said intermetallic $Si_2Al_2Ca$ phase.

3. A metallurgical silicon comprising a crystalline phase of primary silicon having a dissolved phosphorus content between 30 and 150 ppm by weight and intermetallic phases in an amount of 0.5 to 2% by weight, said metallurgical silicon containing from 30 to 180 ppm by weight total phosphorus and not more than 0.3% by weight of an intermetallic $Si_2Al_2Ca$ phase, said silicon containing Al, Ca and Fe in a weight ratio (Al+Ca)/Fe which is between 0.5 and 0.9 and in a weight ratio Al/Ca which is between 2.4 and 4.5.

4. Silicon according to claim 3, wherein (Al+Ca)/Fe is between 0.5 and 0.7.

5. Silicon according to claim 3, wherein (Al+Ca)/Fe is between 0.7 and 0.9.

6. Silicon according to claim 3, wherein Al/Ca is between 3.3 and 3.7.

7. A process for the preparation of metallurgical silicon comprising a crystalline phase of primary silicon having a dissolved phosphorus content between 30 and 150 ppm by weight and intermetallic phases in an amount of 0.5 to 2% by weight, said metallurgical silicon containing from 30 to 180 ppm by weight total phosphorus and not more than 0.3% by weight of an intermetallic $Si_2Al_2Ca$ phase, comprising the steps of:

a) adjusting the amount of phosphorus in raw silicon in the liquid state to 30 to 180 ppm by weight; and b) solidifying the liquid raw silicon to solid metallurgical silicon either at a slow solidification speed of between 6 and 30° C./min between 1000° and 800° C., or at a rapid solidification speed of between 30° and 120° C./min between 1000° and 800° C., and limiting the formation of an intermetallic $Si_2Al_2Ca$ phase in the solidified silicon by 1) adjusting amounts of aluminum, calcium, and iron in the raw silicon such that the weight ratio (Al+Ca)/Fe is between 0.7 and 0.9 for a slow solidification speed, or between 0.5 and 0.7 for a rapid solidification speed; and 2) adjusting amounts of aluminum and calcium in the raw silicon such that the weight ratio Al/Ca is between 2.5 and 4.5.

8. Process according to claim 7, wherein aluminum and calcium are adjusted such that Al/Ca is between 3.3 and 3.7.

* * * * *